United States Patent [19]

Monte et al.

[11] 4,447,527

[45] May 8, 1984

[54] SINGLE TEST FORMULATIONS FOR ENZYME IMMUNOASSAYS AND METHOD FOR PREPARATION

[75] Inventors: Alex A. Monte, Cupertino; Joan G. Centofanti, San Carlos, both of Calif.

[73] Assignee: Syva Company, Palo Alto, Calif.

[21] Appl. No.: 350,897

[22] Filed: Feb. 22, 1982

Related U.S. Application Data

[63] Continuation of Ser. No. 183,131, Sep. 2, 1980, abandoned.

[51] Int. Cl.$^3$ ............................................. G01N 33/54
[52] U.S. Cl. ...................................... 435/7; 435/187; 435/188; 436/536; 436/537
[58] Field of Search ........................ 435/6, 7, 188, 187, 435/805, 810; 436/500, 521, 536, 537, 543, 544, 547, 808

[56] References Cited

U.S. PATENT DOCUMENTS

| | | | |
|---|---|---|---|
| 3,655,838 | 4/1972 | Price et al. ........................... | 435/7 X |
| 3,862,302 | 1/1975 | Price et al. ........................... | 436/521 |
| 3,950,133 | 4/1976 | Monte et al. ......................... | 435/187 |
| 4,017,597 | 4/1977 | Reynolds . | |
| 4,169,012 | 9/1979 | Dawson et al. ........................ | 435/7 |
| 4,190,496 | 2/1980 | Rubenstein et al. .................. | 435/7 |
| 4,218,335 | 8/1980 | Mochida et al. ...................... | 435/7 |
| 4,230,805 | 10/1980 | Singh et al. ........................... | 435/7 |

FOREIGN PATENT DOCUMENTS

| | | | |
|---|---|---|---|
| 2346719 | 9/1977 | Fed. Rep. of Germany . | |
| 2388275 | 12/1978 | France ................................. | 435/188 |
| 2032619 | 5/1980 | United Kingdom ................ | 436/500 |

*Primary Examiner*—Sidney Marantz
*Attorney, Agent, or Firm*—Bertram I. Rowland

[57] ABSTRACT

Reagent mixtures for single test which allow for rapid determination of drugs without sophisticated equipment. Into a single vial as dry powders are combined an enzyme bound ligand reagent, an antiligand reagent (antibody), appropriate substrates, bulking agents, as well as other additives. Upon addition to the reagent mixture of an appropriate volume of diluent and the sample suspected of containing the drug, optionally subject to prior treatment and/or dilution, the reagents are activated and either a single reading at a predetermined time interval or two or more readings over a predetermined time interval are taken of spectrophotometric changes in the solution. By comparison to a standard, the concentration of the drug may be determined quantitatively.

9 Claims, No Drawings

SINGLE TEST FORMULATIONS FOR ENZYME IMMUNOASSAYS AND METHOD FOR PREPARATION

CROSS-REFERENCE TO RELATED APPLICATIONS

This is a continuation of application Ser. No. 183,131, filed Sept. 2, 1980, abandoned.

BACKGROUND OF THE INVENTION

There is a continuing need for simple, rapid and accurate qualitative and quantitative determinations of biologically active substances at extremely low concentrations. The purpose of such determinations can be extremely varied, however there is a particular need today for rapid determinations in doctors' offices, police stations, clinics and laboratories for determining the presence of drugs or narcotics in bodily fluids such as saliva, blood or urine. Therefore, there is a need for methods which do not require sophisticated equipment and which need not be conducted by specially skilled technicians. The classical methods of determining the presence of trace amounts of chemicals or drugs have not been satisfactory in meeting these needs. Thin layer chromatography has a number of deficiencies in that it is slow, requires a high degree of proficiency, and is subject to a wide range of interfering materials. Both gas phase chromatography and mass spectroscopy require sophisticated and expensive equipment as well as a high degree of technical skill.

The radioimmunoassay has long been used in clinical laboratories, however it has been prevented from widespread use in offices and other non-laboratory locations due to handling problems and undesirable hazards stemming from the use of radioactive materials. In addition, radioactive materials may be short lived and the separation of the bound and unbound radioactive analogs required in the assay technique is difficult and thus particularly subject to error.

In an effort to obviate these problems, dipstick assays have been developed which provide for color development when the analyte of interest is present. However, dipsticks are subject to many interferences and rarely can give more than a qualitative result.

Therefore, there remains a need for a rapid, accurate and simple diagnostic method requiring relatively unsophisticated equipment allowing for performance by unskilled personnel. In addition, to meet the requirements of convenience, reliability and simplicity, there is a need for a method which employs reagents which are storage stable, desirably under ambient conditions, and readily reconstituted to a homogeneous solution when provided dry or lyophilized. To meet these objectives, it would be desirable to have a single reagent which encompasses all of the necessary active materials for the test. However, since most assay systems for the determination of biologically active substances require the combination of two or more reagents in a liquid phase at the time of determination, it is necessary for a single reagent system to be maintained dry until used in the assay. However, in making a dry, single test reagent it is not possible to accurately and uniformly combine all of the necessary ingredients by measuring out each dry ingredient and combining them in a dry state. The accuracy and reproducibility necessary for an analytical reagent cannot be attained by such a method. Thus, at some point during the preparation of the dry formulation, some or all of the dry ingredients must be dissolved to form one or more solutions in order to achieve accurate measurement and uniform distribution. On the other hand, at the time the assay is performed, it is essential that the dissolution of the active reagents is rapid and that the active ingredients are homogeneously dispersed in order for the rate of dissolution not to become a factor in the observed measurement. Therefore, there has not heretofore been a single test reagent provided in a dry state which when activated by the addition of a liquid was substantially and instantaneously dissolved so as to allow for a reading within a short period of time.

As further background, U.S. Pat. No. 3,876,502 discloses a diagnostic test reagent formulation comprising a solid water soluble anhydrous storage stable mixture containing a reagent capable of participating in a test reaction to effect a measurable change in a test system, and a solid nitrogen containing polyoxyalkylene nonionic surfactant. U.S. Pat. No. 3,817,837 teaches a homogeneous enzyme immunoassay.

SUMMARY OF THE INVENTION

The present invention provides diagnostic reagents as a soluble powder which is combined with an aqueous solution of an analyte for determination of the analyte. The diagnostic reagent includes in a single vial an enzyme bound ligand, a receptor for the ligand, the enzyme substrates, and ancillary reagents, such as bulking agents, buffers, stabilizers, and the like. The reagent is prepared by combining the receptor with bulking agents and ancillary reagents and the enzyme-bound ligand with fillers and other ancillary reagents, mixing the two mixtures with additional additives in an inert organic solvent and then evaporating the solvent.

DESCRIPTION OF THE SPECIFIC EMBODIMENTS

The present invention provides dry water soluble bulk powder reagent formulations for use in single tests for determination of a wide variety of analytes. The formulated powder when mixed with an aqueous solution containing the analyte rapidly dissolves in the aqueous medium to a homogeneous solution providing for an assay medium which results in a change in intensity of an electromagnetic signal normally light, either UV or visible. The dry bulk powder reagents of the present invention comprise an enzyme bound ligand conjugate, antiligand (antibody), enzyme substrates, bulking reagents, and other active and inert additives. In the employment of the reagents for single tests, a spectrophotometric reading may be taken at a predetermined time interval after mixing the reagent in the analyte medium or by taking a set of readings over a predetermined time range after mixing, in order to obtain an optical density or fluorescence value of the medium or the change in optical density or fluorescence over a predetermined time period of the medium, which in turn can be compared to an assay medium having a known amount of the analyte.

ASSAY DETERMINATION

The reagent composition of the subject invention is provided as a powder which contains all of the necessary reagents for the assay determination. When the reagent formulation containing the enzyme bound ligand conjugate, the antiligand (the antibody), and enzyme substrates dissolved in an aqueous solution containing the analyte, the enzymatic activity of the assay medium is related to the concentration of the analyte in the medium. That is, the enzyme bound ligand and the analyte will compete for the antibody. Since the enzymatic activity will be changed, usually diminished or inhibited, when the enzyme bound ligand binds to the antiligand, the enzymatic activity of the solution will be directly related to the amount of analyte present in the assay medium. The enzyme and enzyme substrate are selected so that either the substrate or the end product absorbs light in the ultraviolet or the visible region or fluoresces. Therefore, upon dissolution of the single test powder reagent of this invention in the aqueous solution containing the analyte, one can determine the analyte concentration by measuring the absorption or emission of light.

In carrying out the assay method, one first measures a predetermined amount of a sample suspected of containing the analyte. Generally, for many drugs in physiological fluid, the volume will range from about 25 to 500 μl, usually about 50 to 200 μl. Depending on the initial volume, one may dilute the sample with an appropriate volume of distilled or deionized water to provide the observed final volume. After adding the powdered reagent composition to the analyte solution, the final volume will be about 0.5 to 10 ml, usually about 1 to 5 ml. One then normally waits at least about 0.25 min to about 15 min usually about 0.5 to 5 min, before taking the first reading, which may be the only reading. Any further readings will normally be taken about 0.5 to 60 min after the time of mixing.

In addition to performing an assay for the analyte, it will normally be desirable to perform assays with one or more calibrators, whereby one would obtain either a single value or a plurality of values at different concentrations and graph the concentration of analyte versus the observed values to obtain a standard curve. No specific temperature control is required, as long as the calibrators and the analyte assay determinations are carried out under substantially similar ambient conditions. The temperature range will usually be from about 15° to 40° C.

FORMULATIONS

The formulations are prepared in two stages. In the first stage, the antibody and enzyme are mixed separately with other reagents to form the antibody trituration and the enzyme trituration. The two triturations are then combined with additional reagents under conditions where the activities of the enzyme and antibody are retained, while preventing binding of the antibody to the enzyme conjugate. The result is a formulation which when mixed with the sample rapidly dissolves and reconstitutes active reagents for an accurate determination of the analyte.

To some degree, the choice of components included in the antibody trituration and the enzyme trituration is arbitrary. Since the active components, antibody and enzyme, are present in extremely small percentages, it will generally be desirable to combine other components with each of the active reagents to minimize mechanical losses of the active reagents. Therefore, it will usually be convenient for some of the components to be split, a portion being combined with the antibody and a portion being combined with the enzyme reagent. Furthermore, by first preparing the two triturations, one can homogeneously disperse the active reagents with the other components of the trituration. This aids in the homogeneous dispersion of the active reagents in the final formulation.

In addition to the antibody and enzyme conjugate, other components which may be included in the triturations are polysaccharidic bulking agents, inert protein, buffers, and stabilizing agents, such as biostats and biocides.

The amount of antibody and enzyme conjugate in the triturations will be based on the amount required per test. Therefore, these two components will be a very small weight percentage of the total weight of the individual triturations and final formulation. Furthermore, these components will vary in accordance with their activity and their final ratio to provide for optimization of the assay sensitivity.

By virtue of preparing the two triturations, prior to final formulation, one can optimize the ratio of the antibody trituration to the enzyme conjugate trituration to provide for the desired sensitivity for the analyte range of interest. Thus, the subject process provides for flexibility during the preparation of the reagent formulation to enhance the sensitivity of the assay. In accordance with the subject process, the processing during final formulation does not adversely affect the reagents in such a way to significantly modify the sensitivity of the assay.

The trituration formulations will for the most part come within the following ranges:

TABLE 1

| | Ranges (wt %)* | | |
|---|---|---|---|
| | Broad | Narrow | Preferred |
| Antibody trituration Component | | | |
| Antiserum | 0.005–0.5 | 0.01–0.2 | 0.02–0.1 |
| Buffer | 0; 1–20 | 0; 1–10 | 1–5 |
| Stabilizer(s) | 0; 0.001–1 | 0; 0.05–0.5 | 0.1–0.5 |
| Neutral salt | 0–20 | 0–15 | 0 |
| Bulking agent(s) | 70–98 | 80–95 | 85–95 |
| Protein | 0–10 | 0; 2–8 | 3–7 |
| Substrates | 0–15 | 0–12 | 0 |
| Enzyme trituration Component | | | |
| Enzyme conjugate | 0.0005–0.05 | 0.001–0.05 | 0.001–0.01 |
| Buffer | 0; 1–20 | 0; 1–10 | 1–5 |
| Stabilizer(s) | 0; 0.001–1 | 0; 0.05–0.5 | 0.1–0.5 |
| Neutral salt | 0–10 | 1–10 | 2–7 |
| Bulking agent(s) | 70–98 | 80–95 | 80–90 |
| Protein | 0–10 | 0; 2–8 | 3–7 |

*0; intends that none of the component need be present but when present will be in the indicated range.

The final formulation will be a combination of the two triturations, any additional reagents which are required, which may include augmenting reagents included in the triturations, as well as additional bulking agent. Particularly, substrates and buffer may be added in combination with the additional bulking agent. For the most part, the final formulation will have the following composition.

TABLE 2

| | Ranges (wt %)* | | |
|---|---|---|---|
| Component | Broad | Narrow | Preferred |
| Antibody | $5 \times 10^{-6}$–0.2 | $1 \times 10^{-5}$–0.05 | $1 \times 10^{-4}$–0.02 |
| Enzyme conjugate | $5 \times 10^{-6}$–0.1 | $1 \times 10^{-5}$–0.05 | $5 \times 10^{-4}$–0.02 |
| Bulking agent(s) | 45–95 | 50–85 | 50–80 |
| Buffer | 5–30 | 5–25 | 10–20 |
| Stabilizer(s) | 0–2 | 0.001–0.5 | 0.01–0.1 |
| Substrates | 1–15 | 1.5–12 | 2–10 |

TABLE 2-continued

| Component | Ranges (wt %)* | | |
|---|---|---|---|
| | Broad | Narrow | Preferred |
| Neutral salt | 2–20 | 2–15 | 4–15 |
| Non-ionic detergent | 0.1–5 | 0.1–2 | 0.2–2 |
| Protein | 0–5 | 0.05–2.5 | 0.1–2 |

METHOD OF PREPARATION OF FORMULATION

In preparing the formulation, the two triturations are first prepared. A first solution is prepared by combining the protein, polysaccharide bulking agent, buffer and stabilizers to the desired concentration. To the aqueous solution is then added a sufficient amount of antibody based on the number of tests to be performed when employing the final formulation.

The procedure is repeated for the enzyme conjugate reagent, except that neutral salt will normally also be included in the enzyme conjugate solution. Again, enzyme conjugate is added in sufficient amount to the solution to provide for the equivalent number of tests provided by the antibody. Aliquots of the solution are then taken and assays performed to insure that the materials are active and a reasonable ratio of enzyme conjugate and antibody is present.

The antibody reagent solution and the enzyme conjugate reagent solution are then independently lyophilized and bottled under inert conditions. The lyophilized material is then pulverized and screened, so that the powder is relatively evenly sized, generally passing through a 40-mesh screen, more preferably passing through a 60-mesh screen. To each of the individual reagent powders is then added a small proportion of the total bulking agent and the mixture blended to provide for substantial homogeneity. These powder compositions are referred to as the triturations.

The triturations are then tested to determine the optimum ratio of the antibody and enzyme conjugate for the range of interest. This is achieved by combining aliquots of the two triturations with substrates, an appropriate amount of bulking agent, and determining the concentration of analyte from samples of calibrators having known amounts of analyte. Once the ratio of antibody to enzyme conjugate has been optimized, the two triturations may then be combined with the additional reagents to provide the final formulation. The amount of each of the triturations will be modified in accordance with the optimization determination.

The two triturations are combined in combination with the additional bulking agent, normally a polyol, usually a reduced sugar of from 5 to 6 carbon atoms, any additional buffer, and any additional substrates. The materials are conveniently mechanically mixed to provide a relatively homogeneous mixture. A halohydrocarbon of from 1 to 3, usually 1 to 2 carbon atoms, particularly chlorocarbons, having at least two chlorine atoms, preferably having at least two chlorine atoms on the same carbon atom is then dispersed into the powder mixture. The amount of the halohydrocarbon will be generally minimized, being not more than about 50 weight percent of the total mixture, usually not more than about 40 weight mixture of the total mixture, generally requiring about 25 weight percent, more usually requiring about 30 weight percent.

In addition to the halohydrocarbon, a nonionic detergent will also be included in minor amount. Particularly, polyalkyleneoxy compounds are employed. The amount of nonionic detergent will be sufficient to provide the desired weight range in the final dry formulation. Conveniently, the nonionic detergent may be added as a solution in a portion of the halohydrocarbon solvent while mixing the dry ingredients followed by the addition of the remaining amount of the halohydrocarbon solvent. The mixing is continued for a sufficient time to insure homogeneity, generally not exceeding 1 hr., more usually not exceeding 0.5 hr., while the temperature is maintained below about 60°, more usually below about 50° C.

The volatiles are then removed in vacuo at temperatures not exceeding about 60° C., preferably not exceeding about 50° C., preferably ambient temperature (20°–25° C.) until substantially all of the volatile material has been removed to provide a dry granulated mixture. Periods of up to about 24 hrs. may be required. To provide an appropriately sized powder, the dry material is then screened through an appropriate mesh screen, generally not greater than about 40-mesh, desirably about 60-mesh and the resulting screened powder will be further blended in conventional blenders for up to about 30 mins. During this time, the material is maintained in a dry environment. The blended material is now ready for packaging in appropriate sealed containers.

MATERIALS

Enzyme bound ligand.

The enzyme bound ligand is amply described in U.S. Pat. No. 3,817,837, which is incorporated herein by reference in its entirety. Particular reference is made to column 6, line 69 though column 26, line 18 for a description of appropriate ligands. Particular reference is made to columns 26, line 20 through column 30, line 67 for a description of appropriate enzymes. The linking groups for the enzymes and ligands are conventional and are amply described in the aforementioned patent as well as numerous other publications.

Among enzymes of particular interest are the hydrolases, particularly lysozyme, cholinesterase, and glycosidases, e.g. β-galactosidase, and the oxidoreductases, particularly dehydrogenases, e.g. malate dehydrogenase and glucose-6-phosphate dehydrogenase, peroxidase, glucose oxidase, or the like.

The ligands will be haptens or antigens, particularly drugs used for therapy, hormones, immunoglobulins, physiological compounds diagnostic of diseased states, or the like.

Various groups of compounds of interest include aralkylamine drugs, where the aryl group is separated from the amine nitrogen by an aliphatic chain of from about 2 to 3 carbon atoms, steroids, amino acids, particularly polyiodothyronines, aminoglycosides, barbituric acid derivatives, phenothiazines, dibenzazepines, benzodiazepines, purines, pyrimidines, and fused polycyclic compounds, such as cocaine and quinidine.

The protein which is added to inhibit matrix effects and enhance the stability of the protein reagents will for the most part be albumins, other than human albumin.

The bulking agents are primarily polyols, which may be sugars or reduced sugars, monomers or polymers. Usually, a combination of polyols will be employed, using a minor amount of a polymeric polyol and a major amount of a monomeric polyol.

The polymeric compounds may be varied widely, conveniently being a polyglucose, such as Dextran. The polymer will generally range from about 10,000 to about 500,000 molecular weight, more usually from about 25,000 to about 200,000 molecular weight. The polymeric bulking agent will generally be from about 0.1 to 5 weight percent of the final composition, more usually from about 0.2 to 2 weight percent of the final composition. In relation to the monomeric bulking agent, the polymeric bulking agent will generally range from about 0.2 to 7 weight percent, more usually from about 0.2 to 3 weight percent.

The monomeric polyol will generally be a reduced sugar of from 5 to 6 carbon atoms. Illustrative polyols include mannitol, xylitol, glucitol, and sorbitol.

The bulking agent should not significantly enhance the viscosity of the assay medium. Furthermore, the bulking agent(s) should rapidly dissolve and aid in the dissolution and dispersal of the active reagents. The bulking agents should be relatively inert, and not adversely affect the properties of the active agents.

The buffers employed are not critical to this invention, and one or another buffer may be employed depending upon the specific reagents. For the most part, buffers include tris with an acid, such as hydrochloric or maleic acid, barbitals, phosphates, carbonates, and the like. Tris is preferred with dehydrogenases. The buffer will provide a pH in the range of 5 to 10, usually 6 to 10.

In view of the fact that the active reagents are proteins, various bacteriostats or bacteriocides which are compatible with the other materials in the formulation may be employed as stabilizers. Common additives include sodium azide and mercury salts, such as Thimerosal. The choice of the particular stabilizer will depend upon the absence of any deleterious effect on the assay, its solubility in water, and the ease with which it may be formulated with the other components.

The substrates will depend upon the particular enzyme, conventional or synthetic substrates normally being employed with the enzymes.

A neutral salt will normally be employed to provide the desired ionic strength. Generally, this will be sodium chloride.

The nonionic detergent may be varied widely, normally being a polyalkylene oxide, where the alkylene group is of from 2 to 3 carbon atoms, and the molecular weight will generally range from about 1,000 to 30,000, more usually from about 2,000 to 10,000. Illustrative nonionic detergents include PEG6000, PEG4000, PEG6000 monostearate, and the like.

By employing the compositions of the subject invention, one can provide a complete formulation in a single vial, which only requires the addition of sample to the formulation. The sample may be used directly or be pretreated. The formulation then rapidly dissolves into the sample solution and after a predetermined time period, one or more readings may be taken as indicative of the amount of analyte in the sample.

In order to demonstrate the ease and efficiency of the subject invention, a number of reagents were prepared and their use in assaying for a variety of drugs determined. The following lists the formulations for reagents for determining a number of different analytes, indicating the combinations of Reagent A (antibody reagent) and Reagent B (enzyme conjugate reagent) and the manner in which the final formulation was prepared. Included in the table are the compositions of the solutions of Reagent a and Reagent b which are lyophilized to prepare Reagents A and B.

TABLE 3[1]

| Reagent a | wt % | Reagent b | wt % |
|---|---|---|---|
| RSA[3] | 2 | RSA | 2 |
| Dextran (70,000 m.w.) | 2 | Dextran (70,000 m.w.) | 2 |
| Sodium azide | 0.1 | Sodium azide | 0.1 |
| Thimerosal | 0.01 | Thimerosal | 0.01 |
| Antibody | —[2] | NaCl | 1.8 |
|  |  | Enzyme conjugate | —[2] |

[1]Reagent a is a solution in 1l of Trizma buffered, pH 8.3 deionized water containing sufficient antibody for about 40,000 tests. Reagent b is a solution in 1l of Tris buffered, pH 8.0 deionized water containing sufficient enzyme conjugate for about 40,000 tests.
[2]Before dissolving the antibody and enzyme conjugate in the buffered media, the reagents are used in assays for the analyte to determine the optimal amount for the assay.
[3]RSA - rabbit serum albumin The reagents are lyophilized in separate pans at a depth not exceeding about ⅝″ and when the cycle is completed, the pans are removed from the lyophilizer under nitrogen and the reagents stored in a dry environment. The reagents are then independently pulverized in an analytical mill for about 30 secs, and then passed through a 60-mesh screen.

Dried mannitol which has been screened through a 60-mesh screen is then combined with the pulverized screened reagents and the individual reagents blended for 5 mins. to provide the powder triturations. The powder triturations will have the following compositions.

TABLE 4

| Antibody trituration | | Enzyme trituration | |
|---|---|---|---|
| Component | mg/test | Component | mg/test |
| RSA | 0.5 | RSA | 0.5 |
| Dextran (70,000 mw) | 0.5 | Dextran (70,000 mw) | 0.5 |
| Trizma base | 0.333 | Trizma base | 0.333 |
| NaN$_3$ | 0.025 | NaN$_3$ | 0.025 |
| Thimerosal | 0.0025 | Thimerosal | 0.0025 |
| Antibody[1] | ~0.005 | Enzyme conjugate[1] | ~0.0005 |
| Mannitol | 8.64 | Mannitol | 8.19 |
|  |  | NaCl | 0.45 |
| Total | 10.0 |  | 10.0 |

[1]Weight not included in the calculation

A substrate solution for the enzyme glucose-6-phosphate dehydrogenase was then prepared by combining 900 mg of NAD and 634 mg of glucose-6-phosphate in 300 ml deionized water and aliquots of the triturations in different amounts employed for determining the enzyme rate in the presence of added mannitol in an amount to simulate the mannitol concentration in the final formulation.

Additional buffer is prepared by combining 12.06 parts of tris base, 8.91 parts of tris-HCl and 15 parts of sodium chloride and the mixture pulverized, screened with a 60-mesh screen and dried. The final formulation is now prepared by combining the antibody trituration, the enzyme trituration, the substrates, the buffer and additional mannitol. In each instance, the specific amounts of the triturations will be empirically determined by performing the assays with the triturations and determining the maximum rates. Normally, the maximum rate will generally vary from about 300 to 600 $\Delta OD$ between the first minute and the second minute after dissolution in enzyme diluent. The diluent contains 0.5% RSA, 1.0% sodium chloride, 0.05% sodium azide, and 0.005% Thimerosal, in 0.11 M tris, pH8.0. When performing the testing prior to mixing the final formulation, the antibody will be diluted with a solution 4.52 mM NAD, 7.5 mM G6P, 0.05 weight percent sodium azide and 0.005 weight percent Thimerosal. In the exemplification below, the desired ratio of antibody trituration to enzyme trituration was 1 to 1. The following ingredients were then combined, placed in a suitable mixing bowl and mixed with a suitable mixer at low speed for 5 mins.

TABLE 5

| Component | mg/test |
|---|---|
| Antibody trituration | 10.0 |
| Enzyme trituration | 10.0 |
| NAD | 4.5 |
| G6P | 3.2 |
| Buffer | 36.0 |
| Mannitol | 61.3 |
| Total | 125.0 |

To 1875 g of the above mixture was added 15 g of PEG6000 and 400 ml methylene chloride while mixing. After the addition, mixing was continued for 5–10 mins. and an additional 500 ml of methylene chloride added. The granules were then distributed in stainless steel trays with the depth not exceeding ¾". The trays were then dried in a vacuum oven for at least about 15 hrs. at room temperature with a pressure of about 28" mercury. After the methylene chloride had completely evaporated, the pans were removed from the oven and screened through a 60-mesh screen in a dry environment. The screened material was blended in a suitable container for 10–15 mins. and then stored in desiccated containers in preparation for vial filling.

Following the above procedure, and using the enzyme glucose-6-phosphate dehydrogenase, formulations were prepared for amphetamine, barbiturate, benzodiazepine, and morphine. The vials employed have rubber stoppers and the results were obtained with a Gilford Stasar III spectrophotometer, and Spectronic 21 reading at 340 nm. The assay is performed by introducing 50 µl of the sample or control standard, followed by 3 ml of water, shaking the vial, introducing the vial into the spectrophotometer taking one or two readings from the time of mixing.

In each instance, it was found that the reagents retained substantially all of their activity during the preparation of the final formulation. The formulation rapidly reconstituted in water, so that readings with samples could be taken within relatively short times to determine the concentration of the analyte. The formulations were particularly useful where the sole interest was whether the analyte was present above some minimum concentration. Cross-reactivity was shown to be substantially the same as the cross-reactivity observed when the same reagents were employed for a commercial assay sold under the EMIT trademark.

Illustrative of the experience with the various analytes urine samples were obtained which had previously been assayed by RIA for morphine. A direct comparison was made between a commercially available homogeneous enzyme immunoassay and the subject assay. Of 124 samples employing a 0.3 µg/ml morphine cutoff and 0.5 µg/ml detection limit, 84 were found to be positive by both tests, 37 were found to be negative and there were 3 discrepancies. These results differed from the 99 samples determined as positive by RIA, which had been done at a different time by a different laboratory.

The experience with morphine and the other analytes demonstrated at least 95% confidence levels as compared to spiked samples with a known concentration of morphine at the detection level.

The subject invention provides for compositions which allow rapid simple tests for determining a wide variety of analytes. The formulations provide a high degree of reliability and accuracy, have long shelf lives, and can easily be used by non-technical personnel. Conventional equipment can be employed and where two tests can be carried out simultaneously, a control and the sample, so that the conditions for the two assay media are the same, one can avoid stringent temperature controls.

Although the foregoing invention has been described in some detail by way of illustration and example for purposes of clarity of understanding, it will be obvious that certain changes and modifications may be practiced within the scope of the appended claims.

What is claimed is:

1. A dry powder formulation capable of uniform dissolution upon mixing with water useful for performing a single assay of the presence of a ligand in an aqueous sample, which comprises:

| | Wt % |
|---|---|
| Antiserum | $5 \times 10^{-6}$–0.2 |
| Enzyme bound ligand conjugate | $5 \times 10^{-6}$–0.1 |
| Substrates | 1–15 |
| Protein | 0–5 |
| Non-ionic detergent | 0.1–5 |
| Neutral salt | 2–20 |
| Buffer | 5–30 |
| Bulking agent | qs |

2. A dry powder formulation according to claim 1, including from 0.001 to 0.01 weight percent stabilizers, which are bacteriostats, or bacteriocides and from 0.1 to 5 weight percent of a nonionic detergent.

3. A dry powder formulation according to claims 1 or 2, wherein said bulking agent is a mixture of a polysaccharide and a reduced sugar, with the polysaccharide being present in from about 0.1 to 5 weight percent of the total composition.

4. A dry powder formulation according to claim 3, wherein said reduced sugar is mannitol.

5. A dry powder formulation according to claim 1, wherein said enzyme bound ligand conjugate is a hapten conjugated to glucose-6-phosphate dehydrogenase.

6. A dry powder formulation according to claim 1, wherein said enzyme bound ligand conjugate is a hapten conjugated to malate dehydrogenase.

7. A dry powder formulation capable of uniform dissolution upon mixing with water useful for performing a single assay of a ligand in an aqueous sample, which comprises:

| | Wt % |
|---|---|
| Antiserum | $1 \times 10^{-4}$–0.05 |
| G6PDH-hapten conjugate | $1 \times 10^{-5}$–0.05 |
| Polysaccharide | 0.2–2 |
| Protein | 0.05–2.5 |
| Buffer | 10–25 |
| Substrates | 2–12 |
| NaCl | 2–15 |
| Nonionic detergent | 0.1–2 |

| | Wt % |
|---|---|
| Mannitol | qs |

8. A dry powder formulation according to claim 7, wherein said buffer is a tris salt and present in an amount to buffer at a pH in the range of about 6 to 10.

9. A method for preparing the formulation according to claim 1 which comprises:

mixing a first powder formulation containing in weight percent of said first powder formulation 0.005-0.5 of the antiserum, 70-98 of the bulking agent, 0-20 of the buffer, and 0-10 of the protein; a second powder formulation containing in weight percent of said second powder formulation 0.005-0.05 of the enzyme bound ligand conjugate, 70-98 of the bulking agent, 0-20 of the buffer, and 0-10 the protein; substrates; any remaining buffer; remaining bulking agent; a non-ionic detergent and a volatile inert halocarbon to provide a homogeneous mixture;

removing the halocarbon in vacuo to provide a granular mixture; and powdering the granular mixture.

* * * * *